United States Patent [19]

Byrnes et al.

[11] Patent Number: 4,868,132

[45] Date of Patent: Sep. 19, 1989

[54] FLUORESCENCE POLARIZATION IMMUNOASSAY FOR AMPHETAMINE/METHAMPHETAMINE

[75] Inventors: Paul J. Byrnes, Libertyville; Cynthia M. Molina, Northbrook; Janis A. Martinus, Wildwood, all of Ill.; Kenward S. Vaughan; Catherine M. Smith, both of Carlsbad, Calif.

[73] Assignee: Abbott Laboratories, North Chicago, Ill.

[21] Appl. No.: 10,355

[22] Filed: Feb. 3, 1987

[51] Int. Cl.$^4$ .......................................... G01N 33/533
[52] U.S. Cl. .................................... 436/546; 436/56; 436/501; 436/808; 436/816; 436/901; 422/61
[58] Field of Search ............... 436/501, 546, 111, 825, 436/56, 808, 816, 901; 422/61

[56] References Cited

U.S. PATENT DOCUMENTS

| | | |
|---|---|---|
| 3,690,834 | 9/1972 | Goldstein et al. . |
| 3,704,282 | 11/1972 | Spector . |
| 3,817,837 | 6/1974 | Rubenstein et al. . |
| 3,856,469 | 12/1974 | Schneider et al. . |
| 3,878,187 | 4/1975 | Schneider et al. . |
| 3,940,475 | 2/1976 | Gross . |
| 3,966,344 | 12/1976 | Gross . |
| 4,016,146 | 4/1977 | Soares . |
| 4,022,878 | 5/1977 | Gross . |
| 4,041,076 | 8/1977 | Avenia et al. . |
| 4,097,586 | 6/1978 | Gross . |
| 4,122,078 | 10/1978 | Yoshioka et al. . |
| 4,255,329 | 3/1981 | Ullman . |
| 4,329,281 | 5/1982 | Christenson et al. . |
| 4,351,760 | 9/1982 | Khanna et al. . |
| 4,420,568 | 12/1983 | Wang, et al. . |
| 4,476,228 | 10/1984 | Huckzermeier et al. . |
| 4,476,229 | 10/1984 | Fino et al. . |
| 4,481,136 | 11/1984 | Khanna et al. . |
| 4,492,762 | 1/1985 | Wang et al. . |
| 4,510,251 | 4/1985 | Kirkemo et al. . |
| 4,585,862 | 4/1986 | Wang et al. . |
| 4,588,697 | 5/1986 | Khanna et al. . |
| 4,593,089 | 6/1986 | Wang et al. . |
| 4,681,859 | 7/1987 | Kramer . |
| 4,751,190 | 6/1988 | Chiapetta et al. . |

FOREIGN PATENT DOCUMENTS

| | | |
|---|---|---|
| 0199042 | 10/1986 | European Pat. Off. . |
| 0201751 | 11/1986 | European Pat. Off. . |
| 0218010 | 4/1987 | European Pat. Off. . |
| 0240021 | 10/1987 | European Pat. Off. . |
| 56-125666 | 3/1980 | Japan . |
| 2111476A | 7/1983 | United Kingdom . |

OTHER PUBLICATIONS

Kanda, Yuko, et al., "Studies on Immunoassay for Methamphetamine, " Japanese Publication 31:3, 14–17, Aug., 1978.

Shipchandler, M. T., et al., "4'-[Aminomethyl] fluorescein and Its N-Alkyl Derivatives: Useful Reagents in Immunodiagnostic Techniques", *Analytical Biochemistry*, 162:89–101 (1987).

Haifman, et al., "Homogeneous, Micelle Quenching Fluoroimmunoassay for Detecting Amphetamines in Urine", Clinical Chemistry, 32/9, 1677–1681 (1986).

(List continued on next page.)

*Primary Examiner*—Christine M. Nucker
*Assistant Examiner*—D. John Griffith, Jr.
*Attorney, Agent, or Firm*—Roberta L. Hastreiter; Alan W. Kowalchyk

[57] ABSTRACT

This disclosure relates to a method and reagents for determining amphetamine and methamphetamine in a biological fluid such as urine. In particular, this disclosure relates to a fluorescence polarization immunoassay procedure for determining the presence of amphetamine and methamphetamine in a single assay and to a novel class of tracer compounds employed as reagents in such procedures. The procedure described includes pretreatment of the biological sample to eliminate cross-reactants such as β-hydroxyphenethylamine by preincubating the sample solely with an aqueous periodate solution having a pH from about 4.0 to about 7.5 without adjustment to an alkaline pH.

16 Claims, 6 Drawing Sheets

OTHER PUBLICATIONS

"Single-Reagent Polarization Fluoroimmunoassay for Amphetamine in Urine", Chemical Abstracts, Vol. 103, 8/26/85, page 8, Abstract No. 64284Y.

Japanese Publication #56-125666.

Single-Reagent Polarization Fluoroimmunoassay for Amphetamine in Urine; D. L. Colbert, G. Gallacher and R. W. Mainwaring-Burton, Clinical Chem. 31/7 1193-1195 (1985).

Amphetamines New Radioimmunoassay; L. T. Cheng, S. Y. Kim, A. Chung and Albert Castro, FEBS Letters; Vol. 36, No. 3; Nov., 1973.

Eramin, S. A., et al., "Single-Reagent Polarization Fluoroimmunoassay of Methamphetamine in Urine", Clinical Chemistry, 33(10): 1903–1906 (1987).

Estimation of β-3,4-Dimethoxyphenethylamine and Related Compounds in Urine Extracts By Radioimmunoassay; Louis J. Riceberg and Helen Van Vunamist Biochemical Pharmacology Vol. 24, pp. 259–265, 1975.

The Radioimmunoassay for Methamphetamine; Chem. Pharm. Bull., 840–842 (1977).

Specificity of an Antibody Directed Against d-Methamphetamine. Studies with Rigid and Nonrigid Analogs Journal of Med. Chem., 1976, Vol. 19, No. 1.

Molina, et al., Clinical Chemistry 31(6):941–942, 1985.

Z= CH₃ OR H

Q – FLUORESCEIN MOIETY OR PROTEIN
T – COUPLING LINKAGE

FIG. 2-A

Q – FLUORESCEIN MOIETY OR PROTEIN
T – COUPLING LINKAGE

FIG. 2-B

X – SEE SPECIFICATION
Z – H OR CH₃

FIG. 2-C

LACTONE ⇌ ACID

FIGURE 4
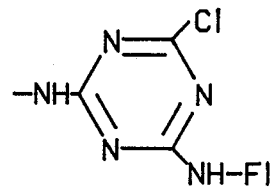
FIG. 4-1
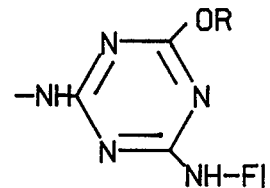
FIG. 4-2
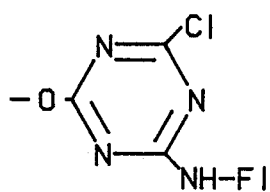
FIG. 4-3
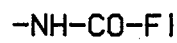
FIG. 4-4
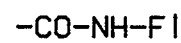
FIG. 4-5
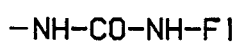
FIG. 4-6
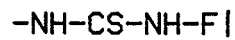
FIG. 4-7
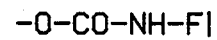
FIG. 4-8
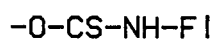
FIG. 4-9
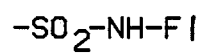
FIG. 4-10
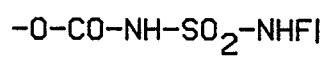
FIG. 4-11

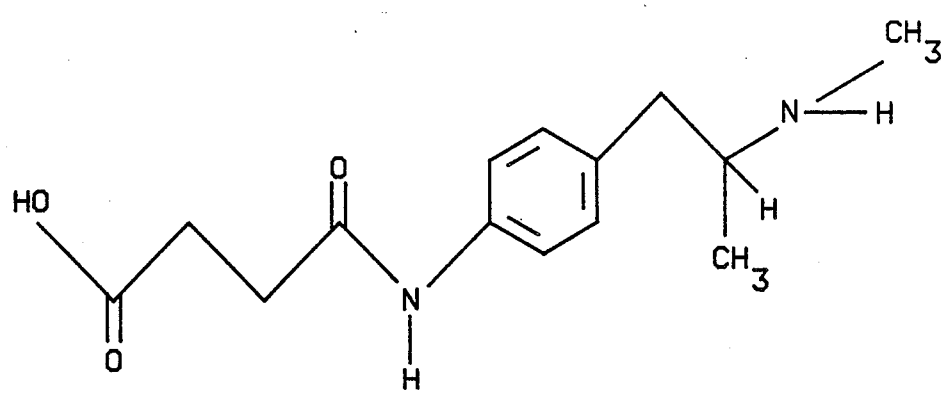
FIG. 9-D
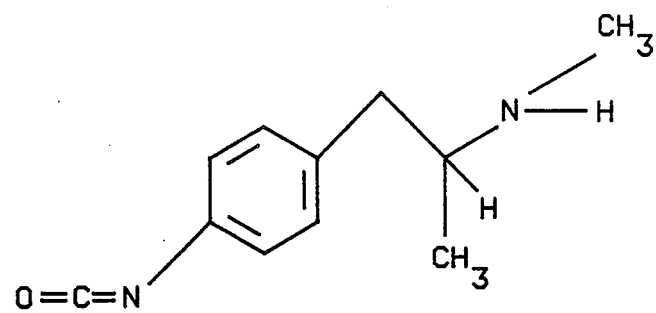
FIG. 9-E
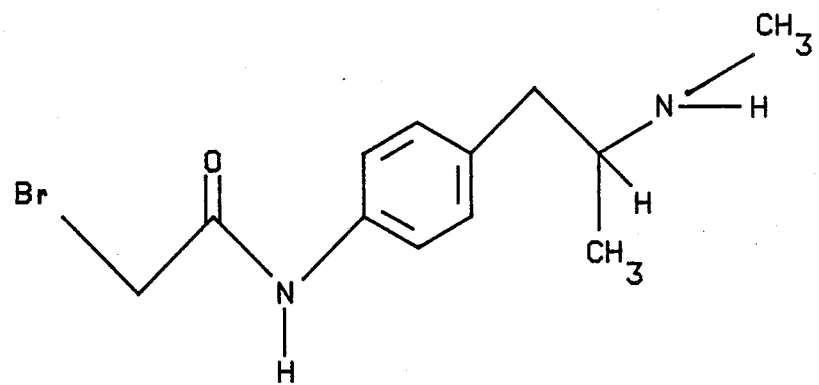
FIG. 9-F

FLUORESCENCE POLARIZATION IMMUNOASSAY FOR AMPHETAMINE/METHAMPHETAMINE

BACKGROUND OF THE INVENTION

1. Technical Field

This invention relates generally to fluorescence polarization immunoassays and reagents useful therein, and particularly to such an assay for amphetamine and methamphetamine. The invention provides a preincubation step which is effective to eliminate cross reactivity to β-hydroxyamines.

2. Background Art

Amphetamine and methamphetamine are sympathomimetic phenethylamine derivatives having central nervous system stimulant activity. These drugs have been used for the treatment of obesity, narcolepsy, and hypotension. Because of their stimulant effects, the drugs are commonly sold illicitly and abused. Physiological symptoms often associated with very high amounts of ingested amphetamine and methamphetamine include elevated blood pressure, dilated pupils, hypethermia, convulsions, and acute amphetamine psychosis.

The biological fluid tested most frequently is urine. Other biological fluids have not been extensively investigated for use in assays for the detection of amphetamine and methamphetamine. In the past, amphetamines have been detected by a number of techniques, including thin-layer chromatography (TLC), gas chromatography (GC), and high performance liquid chromatography (HPLC). These methods generally involve chemical extractions of the drugs, complicated procedures requiring highly trained personnel and lengthy assay times.

In general, competitive binding immunoassays have provided a preferable alternative to chemical methods such as GC and HPLC. Typically, competitive binding immunoassays are used for measuring ligands in a test sample. Generally, a "ligand" is a substance of biological interest to be determined quantitatively by a competitive binding immunoassay technique. The ligands compete with a labeled reagent, or "ligand analog," or "tracer," for a limited number of receptor binding sites on antibodies specific to the ligand and ligand analog. The concentration of ligand in the sample determines the amount of ligand analog which binds to the antibody: the amount of ligand analog that will bind is inversely proportional to the concentration of ligand in the sample, because the ligand and the ligand analog each bind to the antibody in proportion to their respective concentrations.

An accurate and reliable immunoassay requires that antibody "cross-reactivity" (recognition of compounds other than the desired ligand or ligands) be minimized. In the case of assays for amphetamine and methamphetamine it is known that derivatives of β-phenethylamine, such as β-hydroxyphenethylamine compounds, may be strong interferants. One such β-hydroxyphenethylamine, the drug phenylpropanolamine, is found frequently in decongestants sold over the counter. U.S. Pat. No. 3,856,469 discloses removal of β-hydroxyphenethylamine interference from a sample intended for amphetamine or methamohetamine analysis by treating the sample at a pH greater than 8.0 with an amount of aqueous periodate in the presence of ammonium hydroxide. In addition to requiring sample treatment at a basic pH, the aqueous pretreatment in U.S. Pat. No. 3,856,469 is suggested as useful only preceeding sample evaluation by thin layer chromatography and immunoassays by radioimmunoassay, electron spin resonance technique or enzyme technique.

Fluorescence polarization provides an alternative quantitative or qualitative means for measuring the amount of tracer-antibody conjugate produced in a competitive binding immunoassay. Fluorescence polarization techniques are based on the principle that a fluorescent labeled compound, when excited by plane polarized light, will emit fluorescence having a degree of polarization inversely related to its rate of rotation. Accordingly, when a tracer-antibody conjugate having a fluorescent label is excited with plane polarized light, the emitted light remains highly polarized because the fluorophore is constrained from rotating between the time that light is absorbed and emitted. In contrast, when an unbound tracer is excited by plane-polarized light, its rotation is much faster than the corresponding tracer-antibody conjugate and an excited population of molecules is randomized much more quickly. As a result, the light emitted from the unbound tracer molecules is depolarized.

To date no fluorescence polarization assay for determining amphetamine and/or methamphetamine in a single assay has been disclosed.

Accordingly, a need exists for providing a method and reagents for performing a reliable and accurate fluorescence polarization assay for both amphetamine and methamphetamine in biological fluids such as urine. A further need exists for conducting aqueous periodate pretreatment of urine samples to be tested for amphetamine and/or methamphetamine without the addition of pH raising constituents, such as bases.

SUMMARY OF THE INVENTION

The present invention relates to a method for determining amphetamine and methamphetamine utilizing fluorescence polarization techniques. In particular the method of the present invention involves preincubation of a urine sample to be tested for amphetamine and/or methamphetamine without adjustment of the sample's pH to alkaline conditions. Particularly, a sample is treated solely with an aqueous periodate solution, having a pH from about 4.0 to 7.5, to eliminate undesirable compounds which cross-react with antibodies specific for amphetamine and methamphetamine and the ligand analogs thereof.

The treated sample is intermixed with a composition comprising first fluorescein or fluorescein derivative tracer compound coupled to a ligand analog of amphetamine, a second fluorescein or fluorescein derivative tracer compound coupled to a ligand analog of methamphetamine and a first antibody capable of specifically recognizing and binding amphetamine and the first tracer compound and a second antibody capable of specifically recognizing and binding methamphetamine and the second tracer compound. The amount of the first and second tracer compounds bound to the first and second antibodies, respectively, is determined by fluorescence polarization techniques as a measure of the amount of amphetamine and methamphetamine in the sample. The first tracer compound is preferably of the formula:

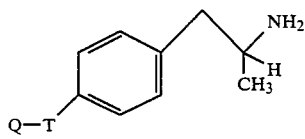

and the second tracer compound is preferably of the formula

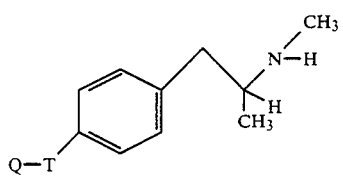

wherein Q is fluorescein or a fluorescein derivative, preferably a carboxyfluorescein or 4'-aminomethylfluorescein, T is a linking group selected from $SO_2$, HN, $HN(CH_3)_3O$, $COCH_2$, $CO(CH_2)_2CONH$, $HN(CH_2)_2$ or $HN(CH_2)_2NHCOCH_2$.

The antibodies to amphetamine and methamphetamine employed in the assay are raised in response to amphetamine and methamphetamine derivatives attached to a protein carrier, preferably bovine serum albumin.

The present invention further relates to a stabilized reagent kit useful for determining amphetamine and methamphetamine in a single assay including a novel fluorescence reagent having tracers of both formulas (I) and (II) and salts thereof, which are useful as reagents in the above-described method. Other components of the reagent kit in accordance with the invention are an aqueous pretreatment solution having an amount of periodate effective in eliminating undesirable cross-reactivity to β-hydroxyphenethylamines and an antibody reagent with a composition comprising a first antibody capable of specifically recognizing and binding amphetamine and a second antibody specifically recognizing and binding methamphetamine. In the case of automated fluorescence polarization assays utilizing automated dispensing means such as a pipette, the present invention provides for a washing of the dispensing means with an aqueous periodate solution to minimize sample carryover resulting from urine adhesion to the dispensing means. The preferred aqueous wash solution is from about 0.1 to 0.25 molar sodium periodate.

Further objects and attendant advantages of the invention will be best understood from a reading of the following detailed description taken together with the drawings and the Examples.

BRIEF DESCRIPTION OF THE DRAWINGS

In the following Figures the symbol "F1" represents a fluorescein moiety, and the various other symbols are noted in the Detailed Description.

FIGS. 2a and 2b show a general structural formula for the tracers and the immunogens of the present invention. FIG. 2c shows a general stuctural formula for the class of reactants used to prepare tracers and immunogens in accordance with the present invention.

FIG. 4 shows various linkages that couple the fluorescein moiety to the precursor in FIG. 2, when

DETAILED DESCRIPTION OF THE INVENTION

Definitions

Figure 1:
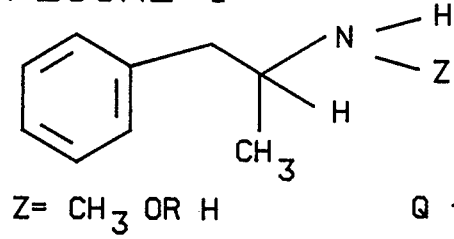
FIG. 1 shows the general structure of the class of phenethylamines to be quantitatively or qualitatively determined in accordance with the present invention.

The term "ligand", as used herein, refers to a molecule, to which a binding protein, such as a receptor or an antibody, can be obtained or formed. The ligands of interest in the present invention are phenethylamines, more particularly, amphetamine and methamphetamine. Such ligands are protein-free compounds, generally of low molecular weight, which do not induce antibody formation when injected into an animal but which are reactive to antibodies. Ligands which are chemically modified for conjugation to a carrier protein are termed haptens. Antibodies to haptens are generally raised by first conjugating the haptens to a protein carrier and injecting the conjugate product into an animal. The resulting antibodies may be isolated by conventional, well-known antibody isolation techniques.

The term "ligand-analog", as used herein, refers to a mono- or polyvalent radical, a substantial portion of which has the same spatial and polar organization as the ligand to define one or more determinant or epitopic sites capable of competing with the ligand for the binding sites of a receptor. A characteristic of such a ligand-analog is that it possesses sufficient structural similarly to the ligand of interest as to be recognized by the antibody against the ligand. For the most part, the ligand-analog will have the same or substantially the same structure and charge distribution (spatial and polar organization) as the ligand(s) of interest (for purposes of the present invention, amphetamine and methamphetamine) for a significant portion of the molecular surface. Frequently, the linking site for a hapten will be the same in preparing the antigen for production of antibodies as that used in the tracer for linking to the ligand, the same portion of the ligand analog which provides the template for the anitbody will be exposed by the ligand analog in the tracer.

The present invention involves the use of fluorescein and derivatives of fluorescein. A necessary property of fluorescein and its derivatives for the usefulness of the tracer compounds herein is the fluoreseence. Fluorescein exists in either of two tautomeric forms, illustrated in FIG. 3, depending on the acid concentration (pH) of the environnment. In the open (acid) form, there are a number of conjugated double bonds which make that form of flourescein (and compounds containing a fluorescein moiety) capable of absorbing blue light and emitting green fluorescence after an excited state lifetime of about 4 nanoseconds. When the open and closed forms coexist, the relative concentration of molecules in the open and closed forms is easily altered by adjustment of the pH level. Generally, the tracer compounds of the present invention exist in solution as salts such as sodium, potassium, ammonium and the like, allowing the compounds to exist in the open, fluorescent form, when employed in the analytical methods of the present invention. The specific salt present will depend on the buffer employed to adjust the pH level. For example, in the presence of a sodium phosphate buffer, the compounds of the present invention will generally exist in the open form, as a sodium salt.

As used herein, the term "fluorescein," either as an individual compound or as a component of a larger compound, is meant to include both the open and closed forms, if they exist for a particular molecule, except in the context of fluorescence. An open form is necessary for the fluorescence to occur.

Figure 3:
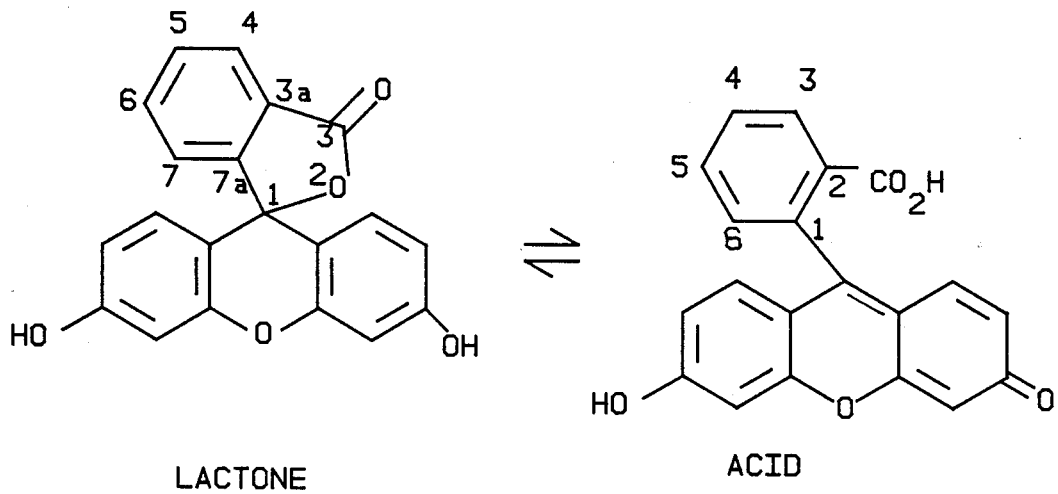
FIG. 3 shows the alternate structural formulae and names of the fluorescein moiety included in the tracers of the present invention.

The numbering of carbon atoms of the fluorescein molecule varies, depending upon whether the open or closed form of the molecule is considered. Accordingly, the literature concerning fluorescein and its compounds is not uniform as to carbon atom numbering. In the closed form, the carbon para to the carboxylic acid group on the phenyl ring is numbered 5. For purposes of this disclosure, the numbering of the closed form (as illustrated in FIG. 3) is adopted because the raw materials used in the syntheses are most popularly numbered with that system. The carbon atom of fluorescein and its derivatives para to the carboxyl group is therefore numbered "6" for the purposes of the present disclosure.

A tracer in solution which is not complexed to an antibody is free to rotate in less than the time required for absorption and re-emission of fluorescent light. As a result, the re-emitted light is relatively randomly oriented so that the fluorescence polarization of a tracer not complexed to an antibody is low, approaching zero. Upon complexing with a specific antibody, the tracer-antibody complex thus formed assumes the rotation rate of the antibody molecule which is slower than that of the relatively small tracer molecule, thereby increasing the polarization observed. Therefore, when a ligand competes with the tracer for antibody sites, the observed polarization of fluorescence of the resulting mixture of the free tracer and tracer-antibody complex assumes a value intermediate between that of the tracer and that of the tracer-antibody complex. If a sample contains a high concentration of the ligand, the observed polarization value is closer to that of the free tracer, i.e., low. If the test sample contains a low concentration of the ligand, the polarization value is closer to that of the bound tracer, i.e., high. By sequentially exciting the reaction mixture of an immunoassay with vertically and then horizontally polarized light and analyzing only the vertical component of the emitted light, the polarization of fluorescence in the reaction mixture may be accurately determined. The precise relationship between polarization and concentration of the ligand to be determined is established by measuring the polarization values of calibrators with known concentrations. The concentration of the ligand can be extrapolated from a standard curve prepared in this manner.

The particular tracers formed in accordance with this invention have been found to produce suprisingly good assays, as will be demonstrated infra.

The Reagents

The objective in designing a Fluorescence Polarization Immunoassay is to have competition between the desired phenethylamines and the tracers for the recognition sites of the antibody. Great variations in the structure of the haptens and tracers are allowed in achieving this goal. For purposes of this invention, "haptens" are precursors of the immunogens or tracers, comprising generally a substituted phenethylamine derivative and a linking group to the protein carrier or fluorescein compound.

1. Pretreatment Reagent

An important aspect of the present invention is the elimination of cross-reactivity to β-hydroxyphenethylamines in a fluorescence polarization assay by pretreating the test sample with an effective amount of an aqueous periodate solution. Specifically, the aqueous periodate solution causes cleavage of the side chain between the α and β-carbon when there is a hydroxy(—OH) attached to the α-carbon. Thus, the compound no longer competes for the binding sites.

The pretreatment reagent in accordance with the reagent kit of the present invention includes an aqueous periodate solution having a pH from about 4 to 7.5. Preferably, the pretreatment solution includes 0.1 to 0.25M of sodium periodate having a pH range from about 4.0 to 5.0. Most preferably the sodium periodate solution includes about 0.125M sodium periodate having a pH of about 4.5. Suprisingly, it has been found that pretreatment of a test sample can be conducted without the need for pH adjustment of the test sample to alkaline conditions with compounds such as hydroxides.

2. The Tracers a. The Structure of the Tracers

Useable tracers can be produced from a wide variety of phenethylamine derivatives. The tracers of the present invention have the general structural formula shown in FIG. 2, where Q represents a fluorescein moiety or a fluorescein derivative.

The tracer is a phenylethylamine derivative that is linked to a fluorescein derivative by, for example, an amido, amidino triazinylamino, carbamido, thiocarbamido, carbamoyl, thiocarbamoyl, or sulfonylcarbamyl group, as shown in FIG. 4. The tracers are prepared by linking the appropiate fluorescein derivative to a phenylethylamine derivative containing an amino, carboxylic acid, hydroxy, imidate, hydrazide, isocyanate, thioisocyanate, chloroformate, chlorothioformate, chlorosulfonyl, or the like group, as will be discussed in the context of the synthetic method and the Examples below.

By way of example, any of the following fluorescein derivatives can be used:

| | |
|---|---|
| Fl—NH$_2$ | fluorescein amine |
| Fl—CO$_2$H | carboxyfluorescein |
| Fl—NHCOCH$_2$I | -iodoacetamidofluorescein |
| Fl—CH$_2$NH$_2$ | aminomethylfluorescein |

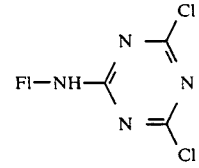

2,4-dichloro-1,3,5-triazin-2-yl amino-fluorescein (DTAF)

-continued

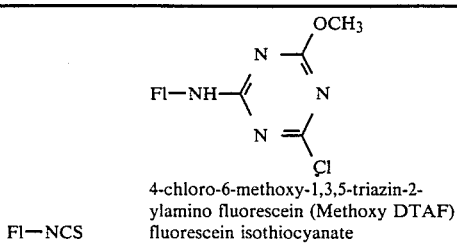

4-chloro-6-methoxy-1,3,5-triazin-2-ylamino fluorescein (Methoxy DTAF)

Fl—NCS  fluorescein isothiocyanate

The preferred tracers in accordance with the present invention are represented by formulas I and II herein. Most preferably the tracers have the structural formula shown in FIGS. 5 and 6 in which carboxyfluorescein and 4'-aminomethylfluorescein are linked to amphetamine and methamphetamine ligand-analogs, respectively.

b. The Synthesis of the Tracers

Figure 2:
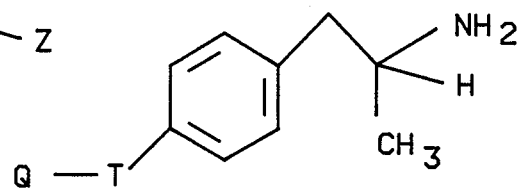
FIG. 2 represents a precursor for the tracers.
Figure 2:
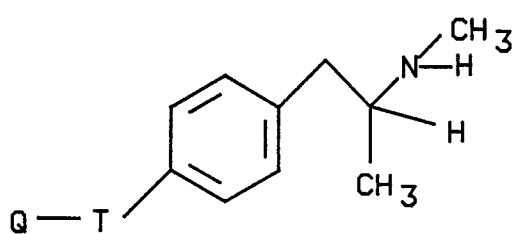
Figure 2:
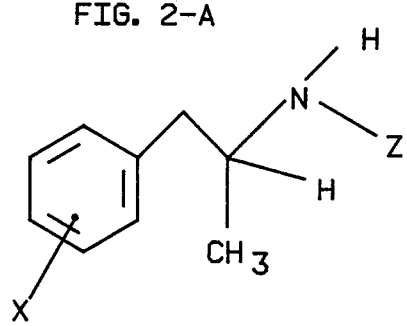

The tracers of the present invention are made by coupling a fluorescein moiety, or a derivative of fluorescein, to the general structure shown in FIG. 2 when X is $NH_2$, COOH, CNOR, OH or $SO_2Cl$.

The fluorescein moiety can be linked to the amino, carboxyl, chlorosulfonyl, imidate or alkoxy functional group by an amide, an amidine, an urea, a thiourea, a carbamate, a thiocarbamate, triazinylamino, sulfonamide, or sulfonylcarbamate linkage, as shown in FIG. 4. In the presently preferred embodiment for amphetamine, the fluorescein derivative is 5-carboxyfluorescein and this is coupled to a precursor of the tracer shown in FIG. 2c. The 5-carboxyfluorescein is coupled to 4-(3-aminopropoxy)-amphetamine (protected on the phenethylamine nitrogen by a t-butoxycarbonyl group) by first forming the active ester of 5-carboxyfluorescein. The preferred active ester is N-hydroxysuccinimide active ester and the preferred method is via N,N'-dicyclohexylcarbodiimide activation in dry pyridine. Other activating groups, such as 1-hydroxybenzotriazole, p-nitrophenol, and imidazole, can be used; and other solvents, such as dimethylformamide and dimethylsulfoxide, can be used. The reactants are preferably coupled under conditions for forming amide linkages, and it is most preferred that active ester procedures be used. The N-BOC group is then removed by brief exposure to an approximately 1:1 solution of $CF_3CO_2H$ and $CH_2CL_2$.

Figure 6:
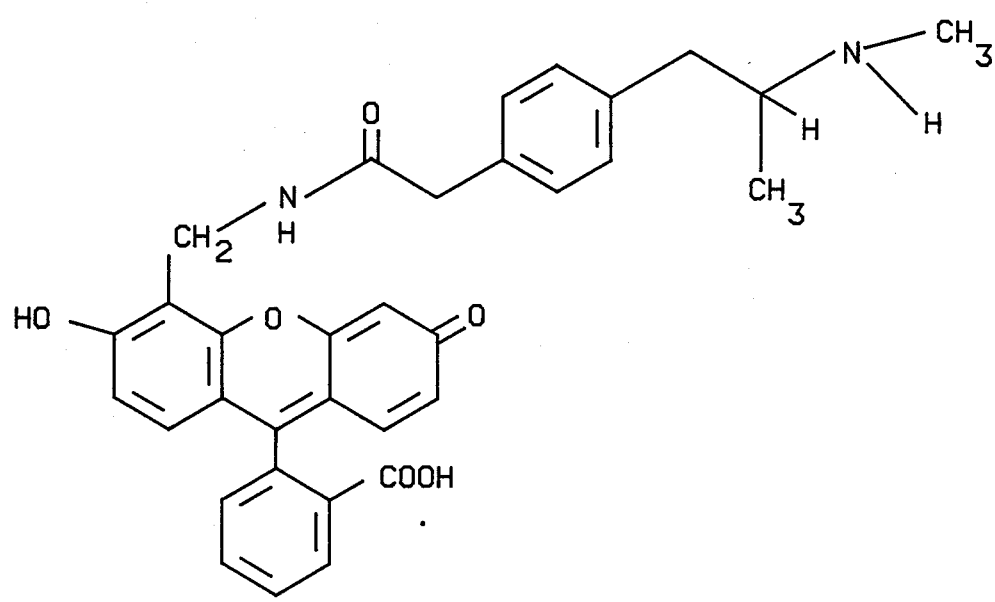

The preferred embodiment for the methamphetamine tracer is shown in FIG. 6, where the fluorescein derivative is 4'-aminomethylfluorecein. This is coupled to a precursor shown in FIG. 2c.

The methamphetamine derivative is converted to its active ester. The preferred active ester is a derivative of 2-ethyl-5-phenylisoxazolium-3'-sulfonate also known as Woodward's Reagent K. Other activating groups, such as 1-hydroxybenztriazole, p-nitro-phenol, carbonyldiimidazole and N-hydroxysuccinimide can be used; and other solvents, such as dimethylformamide and dimethylsulfoxide can be used. The preferred solvent is a mixture of dimethylformamide and triethylamine; other solvents such as pyridine and dimethylsulfoxide can also be used. The reactants are preferably coupled under conditions for forming amide linkages, and it is most preferred that active ester procedures be used. The N-BOC group is then removed by brief exposure to a 1:1 solution of $CF_3COOH$ and $CH_2Cl_2$.

Usable tracers can be prepared from a variety of phenylethylamine derivatives.

All phenylethylamine derivatives that have a terminal amino group, such as amino, hydrazinyl, hydrazido or the like, are coupled to carboxyfluorescein by the active ester method or the mixed anhydride method, and coupled to fluorescein isothiocyanate, DTAF or alkoxy DTAF by simply mixing the two materials in solution. The amino group can be converted to the isocyanate and thioisocyanate groups by reaction with phosgene and thiophosgene, respectively. These are then condensed with fluoresceinamine or 4'-aminomethylfluorescein to produce the tracer.

All phenylethylamine derivatives that have a terminal chlorosulfonyl group are coupled to 4'-aminomethylfluorescein or fluoresceinamine by simply mixing the two materials in solution and using a base to remove the acid that is generated.

All phenylethylamine derivatives that have a terminal carboxylic acid group, such as carboxylic acid, (aminohydroxy)alkylcarboxylic acid or the like, are coupled to 4'-aminomethylfluorescein or aminofluorescein by the active ester method.

c. Combination of Tracers

According to the present invention, the preferred tracer reagent is a composition comprising salts of a first tracer and a second tracer. Generally, the first tracer is a salt of a ligand analog to amphetamine and the second tracer is a salt of a ligand analog to methamphetamine. The combination of individual tracers for amphetamine and for methamphetamine provides the advantage of detection of both drugs (amphetamine/methamphetamine) while maintaining high specificity, low cross-reactivity, high sensitivity and accuracy. Numerous combinations of amphetamine tracers with mehtamphetamine tracers formed in accordance with the above described procedures may be used. Preferably, the first and second tracers are salts of sodium, potassium, ammonium and the like. Most preferably, the first and second tracers exist in the reagent solution as sodium salts and the first tracer is the ligand analog of amphetamine shown in FIG. 5 and the second tracer is the ligand analog of methamphetamine shown in FIG. 6. The tracer formula presently preferred is about 150 nanomolar of the mixed tracers in 0.1 molar sodium phosphate buffer at pH 7.5; 0.1% sodium azide; and 0.01 bovine gamma globulin.

3. The Antibodies

The antibodies of the present invention are prepared by developing a response in animals to the immunogens described below. The immunogen is administered to animals such as rabbits or sheep by a series of injections, in a manner well-known to those skilled in the art.

a. The Structure of the Immunogens

Usable antibodies can be produced from a variety of phenethylamine derivatives. Immunogens prepared from phenethylamine compounds functionalized at the para position shown in FIG. 2, can produce antibodies in animals. Such antibodies are useful in an assay for phenethylamines according to the invention when combined with the appropriate tracer.

The immunogens of the present invention have the general structural formula shown in FIG. 2 and are prepared by coupling a phenethylamine compound of the class shown in FIG. 2 with a protein or a protein derivative, as will be discussed in the context of the synthetic method and the Examples below. The structural formula shown in FIG. 2 is preferred because the best recognition of the desired phenylethylamine compounds occurs when the ring is substituted at a position as distant as possible from the sidechain (i.e., para position).

Figure 7:
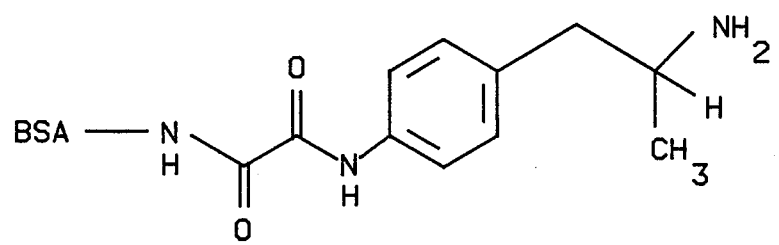
FIGS. 7 and 8 show examples of structures of preferred immunogens used to raise antibodied to amphetamine and methamphetamine in accordance with the present invention.
Figure 8:
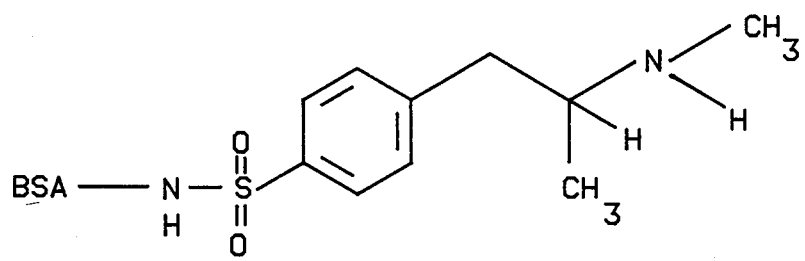

In a preferred form of the invention, the immunogen is prepared by coupling the aforedescribed substituted phenethylamine compound with bovine serum albumin. Various other protein carriers may also be used to good advantage, e.g., keyhole limpet hemocyanin, egg ovalbumin, bovine gamma-globulin, thryoxine-binding globulin, and so forth. Alternatively, synthetic poly(amino acids) having a sufficient number of available amino groups can be employed, as can other synthetic or natural polymeric materials bearing functional groups reactive with amphetamine or methamphetamine haptens. The most preferred immunogens according to the present invention are shown in FIGS. 7 and 8.

b. The Synthesis of the Immunogens

The immunogens of the present invention are made by coupling an amphetamine or methamphetamine derivative to a poly(amino acid) as seen generally in FIG. 2.

Figure 9:
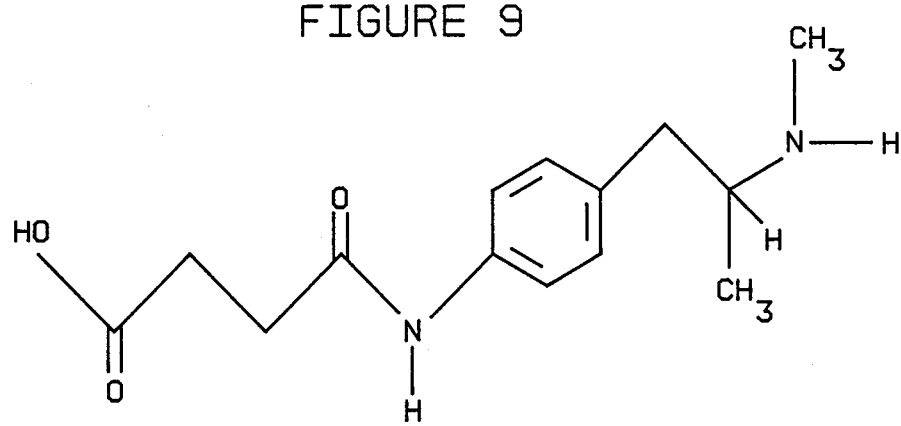
FIGS. 9(a-f) shows exemplary structures of haptens useful to form in accordance with the present invention.
Figure 9:
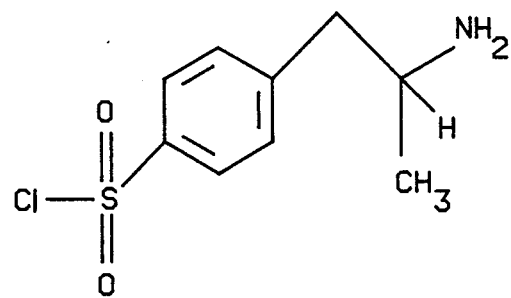
Figure 9:
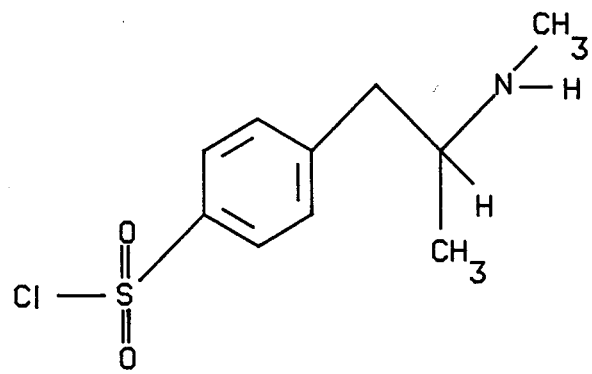

In a preferred embodiment, the poly(amino acid) is bovine serum albumin (BSA), and the hapten can be selected from one of the exemplary structures is FIG. 9 (a-f). These reactants are preferably coupled under conditions normally used to form amide, sulfonamide, urea, and alkylamine linkages, and such conditions are well known to those skilled in the art. It is most preferred when carboxylic groups are employed as a partner in the coupling reaction that active ester procedures be used, as these are the most effective in forming the desired amide linkages in this context.

Before coupling the hapten to the poly(amino acid), the amine on the sidechain is protected. The protecting groups, for example: trifluoroacetyl or BOC (t-butylcarbamate), are added under conditions known to one skilled in the art.

The immunogens are prepared by coupling a hapten, having its phenethylamino group protected and bearing an $-NH_2$, $-CO_2H$, $-CONHNH_2$, $-CNOR$, $-CHO$, $-Br$, $-I$, $-NCO$, $-NCS$, $-OCOCl$, $SO_2Cl$ or $-OCSCl$ group in the para position, to a poly(amino acid). The $-NH_2$ can be coupled by reacting the amine with succinic anhydride, activating the resulting carboxyl group and adding this to the poly(amino acid), or by activating the carboxylic acid group on the polyamino acid in the presence of the $-NH_2$ group. The activation of the carboxylic acid groups on the poly(amino acid) can be accomplished by mixing the hapten and the poly(amino acid) with 1-ethyl-3-(3-dimethylaminopropyl) carbodiimide (EDC), N,N'-dicyclohexylcarbodiimide (DCC), 1-cyclohexyl-3-(2-morpholinoethyl) carbodiimide methyl-p-toluene sulfonate, or the like. The $-CO_2H$ case is also coupled by the activation method (EDC) or the active ester method, as described below in the tracer synthesis section. The $-Br$ and $-I$ cases also produce alkylated amines on the poly(amino acid) but by direct coupling of the alkylhalide to the amine on the poly(amino acid). The sulfonyl chloride, isocyanate ($-NCO$), isothiocyanate ($-NSC$), chloroformate ($-OCOCl$) and chlorothioformate ($-OCSCl$) cases produce sulfonamide, urea, thiourea, carbamate and thiocarbamate linkages, respectively. This is accomplished by direct coupling of the hapten to the poly(amino acid).

After coupling the sidechain amine-protected hapten to the protein, the protecting group is removed to provide the free amine or the amine in a salt form. When the protecting group employed is trifluoroacetyl, it can be removed by treatment with aqueous base, by exposure to aqueous sodium borohydride, or other conditions known to one skilled in the art. When the protecting group is BOC (t-butylcarbamate) it can be removed by aqueous acids, non-aqueous acids, or other procedures known to one skilled in the art.

The syntheses of the above haptens are accomplished in very similar ways. [FIG. 2c shows an immunogen precursor class in accordance with a preferred embodiment of the method of the present invention.] The ideal starting material is a phenylethylamine, such as amphetamine or methamphetamine. The sidechain amine functionality must be rendered unreactive by a protecting group if the X moiety is $SO_2Cl$. If X is $BrCH_2CONH$, $ICH_2CONH$, $ClCONH$, $OCNH$, or $H_2N$, then the protecting group could be introduced before or after the following nitration reaction. Nitration for the latter group of haptens is accomplished by exposure of the protected or unprotected phenylethylamine to cold fuming nitric acid. After catalytic reduction of the nitro group to an amimo group, it is then condensed with succinic anhydride, bromoacetyl bromide, or phosgene (or a phosgene-equivalent). Carboxyl-containing haptens are activated using methods described above. The bromoacetamido derivatives are coupled to protein in the presence of aqueous potassium or sodium iodide. In the case where X is $SO_2Cl$, protein coupling is effected by exposing an aqueous or aqueous-organic solution of protein to the chlorosulfonyl phenylethylamine derivative. After conjugation, the protecting groups are removed by methods known to one skilled in the art, and the immunogens are purified either by size exclusion chromatography or dialysis.

c. Combination of Antibodies

According to the present invention, the preferred antibody reagent is a composition comprising a first antibody raised in response to an immunogen described above, capable of recognizing and binding to amphetamine, and a second antibody, capable of recognizing and binding methamphetamine. Numerous combinations of antibodies raised in response to amphetamine or methamphetamine immunogens, in accordance with the above-described procedures, can be used provided that the antibodies are specific for amphetamine and/or methamphetamine. Most preferably, the antibody reagent includes an amount of the antibody raised in response to the immunogen in FIG. 7 and an amount of the antibody raised in response to the immunogen in FIG. 8.

Rabbit, sheep or any other animal serum can serve as the source of antibodies for the antibody agent. The preferred antisera formula comprises rabbit serum diluted with 0.1 molar sodium phosphate buffer at pH 7.5; 0.1% sodium azide; 0.01% bovine gamma globulin; and 2% ethylene glycol (volume/volume).

4. Wash Reagent

It has been surprisingly determined that providing a phenethylamine fluorescence assay reagent kit with an aqueous periodate wash reagent improves assay reliability and accuracy. Specifically, it has been found that providing a wash solution with about 0.1 to 0.25M aqueous periodate eliminates urine adhesion to dispensing means such as a probe, pipette, or syringe. It is to be understood that urine adhesion to the dispensing means can result in sample contamination yielding false positive results for samples tested subsequent to a phenethylamine-containing sample. In the case of highly automated assaying apparatus, such as the ABBOTT TDx® Clinical Analyzer, which test large numbers of samples sequentially, eliminating urine "carryover" between samples is highly desirable. Preferably, the reagent kit is provided with a wash solution including about 0.125M sodium periodate.

The Assay

The particular tracers and antibodies of the present invention have been found to produce excellent results in fluorescence polarization assays for the desired phenethylamine. FIG. 1 shows the general structure of the class of phenethylamines that can be quantitatively and/or qualitatively determined in accordance with the present invention. For example, one assay of the present invention provides a more rapid and accurate amphetamine/methamphetamine assay method than prior art methods because it requires no specimen treatment before analysis and the assay system has minimal cross-reactivity to amphetamine-like compounds.

The amphetamine/methamphetamine assay, in accordance with the analytical methods of the preferred embodiment of the present invention, involves pretreating a urine sample containing or suspected of containing amphetamine and/or methamphetamine with an effective amount of an aqueous periodate solution having a pH from about 4 to 7.5 for a period of time sufficient to eliminate undesired cross-reactivity. Preferably, the sample is pretreated with 0.1 to 0.25 molar aqueous sodium periodate solution for about 1 to 9 minutes, most preferably 4 to 5 minutes at a temperature range from about 31° to about 36° C.

The pretreated sample is then mixed with tracer and antibody reagents specific to amphetamine and to methamphetamine. Amphetamine or methamphetamine and the tracers compete for limited antibody sites, resulting in the formation of antibody-ligand complexes. By maintaining a constant concentration of tracer and antibody, the ratio of antibody complex to tracer-antibody complex formed upon incubation is directly proportional to the amount of amphetamine and/or methamphetamine in the sample. Therefore, upon exciting the mixture with plane polarized light and measuring the polarization of the fluorescence emitted by a tracer and a tracer-antibody complex, one is able quantitatively or qualitatively to determine the amount of amphetamine and/or methamphetamine in the sample.

The results can be quantified in terms of net millipolarization units, span (in millipolarization units) and relative intensity. The measurement of millipolarization units indicates the maximum polarization when a maximum amount of the tracer is bound to the antibody in the absence of amphetamine or methamphetamine. The amount of tracer bound to the antibody is directly proportional to the net millipolarization. For purposes of the present invention, a net millipolarization value of over 190 is ideal, but a value in the range of about 150 to about 220 is acceptable. The span is an indication of the difference between the net millipolarization at the points of the maximum and the minimum amount of tracer bound to the antibody. A larger span provides for a better quantitative analysis of data. For the purposes of this invention, a span of at least about 60 millipolarization units is preferred. The intensity is a measure of the amplitude of the fluorescence signal that is above the background fluorescence. Thus, a higher intensity will give a more accurate measurement. The intensity is determined for the preferred tracers of the invention as the sum of the vertically polarized intensity plus twice the horizontally polarized intensity. The intensity can range from a signal of about three times to about thirty times the background noise depending upon the concentration of the tracer and other assay variables. For the purposes of the present invention, an intensity of at least eight to ten times that of noise background is preferred.

Figure 5:
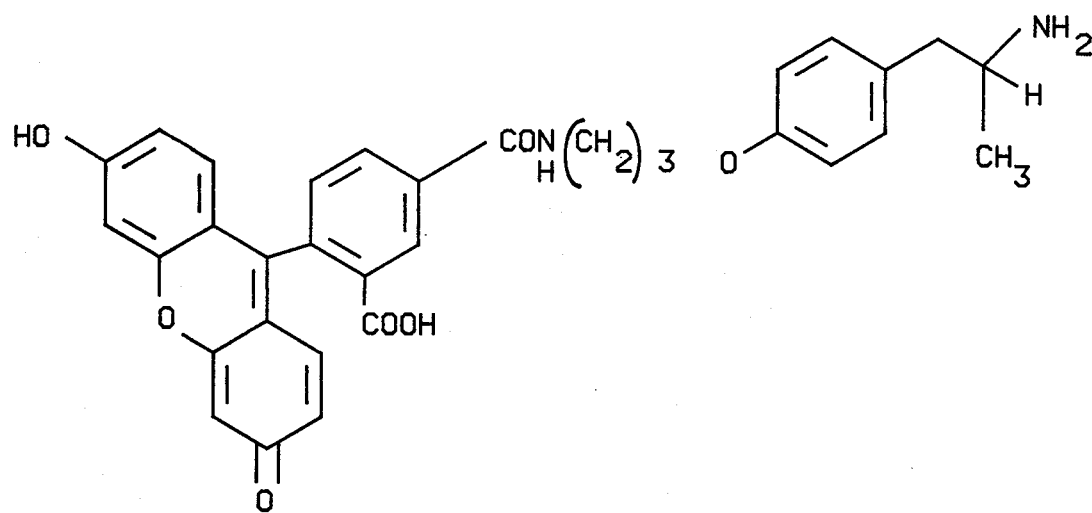
FIGS. 5 and 6 show examples of structures of preferred tracers of amphetamine and methamphetamine in accordance with the present invention.

Table I shows the results obtained with the preferred antibodies raised in response to immunogens (FIGS. 7 and 8) and tracer compounds (FIGS. 5 and 6) of the present invention in terms of span, millipolarization units and intensity. As seen from the data in Table I, an assay using the antibody produced from the immunogen of FIG. 7 in combination with the tracer of FIG. 5 provides excellent results for an amphetamine assay. For assay of methamphetamine, a combination of antisera derived from an immunogen of FIG. 8 with tracer of FIG. 6 provides excellent results.

One aspect of the present assay that is unique is the combination of antisera produced from immunogens 7 and 8 with tracers 5 and 6 to produce an assay with a net polarization of 210 and a span over 70 for either amphetamine or methamphetamine. This is the most preferred configuration of the assay.

TABLE 1

| Hapten Used In Immunogen For Antibody | Tracer | Net Polarization | Span | Intensity |
|---|---|---|---|---|
| FIG. 7 | FIG. 5 | 213.40 | 130.71 | 2365.4 |
| FIG. 8 | FIG. 6 | 190.51 | 126.85 | 2505.9 |

The pH at which the method of the present invention is conducted must be sufficient to allow the fluorescein moiety of the tracers to exist in their open form. The pH may range from about 3 to 12, more usually in the range of from about 5 to 10, most preferably from about 6 to 8. Various buffers may be used to achieve and maintain the pH during the assay procedure. Representative buffers include borate, phosphate, carbonate, tris, barbital and the like. The particular buffer employed is not critical to the present invention, but phosphate buffer is preferred. The cation portion of the buffer will generally determine the cation portion of the tracer salt in solution.

The preferred method of the improved assay of the present invention is discussed in detail in Example 5. The assay is a "homogenous assay," which means that the end polarization readings are taken from a solution in which bound tracer is not separated from unbound tracer. This is a distinct advantage over heterogeneous immunoassay procedures where the bound tracer must be separated from the unbound tracer.

As described previously herein, the reagents for the fluorescence polarization assay of the present invention comprise antibodies specific for amphetamine and methamphetamine, fluorescein tracer analogs of amphetamine and methamphetamine and a periodate pretreatment solution. Additionally, conventional amphetamine/methamphetamine assay solution, including a dilution buffer, d,l amphetamine calibrators and d,l-amphetamine controls are preferably prepared.

The preferred procedure is especially designed to be used in conjunction with the Abbott TDx ® Clinical Analyzer available from Abbott Laboratories, Irving, Tex. It is to be understood that when the Abbott TDx ® Analyzer is used, the assay is fully automated from pretreatment to final reading. However, manual assay can be performed. In the case of automated and manual assays, the sample is mixed with the pretreatment solution in dilution buffer and a background reading is taken. The tracer is then mixed with the assay. The antibody is then finally mixed into the test solution. After incubation, a fluorescence polarization reading is taken and processed. In the case of both manual and automated assays, the present method eliminates the need for sample pH adjustment.

EXAMPLE 1

Preparation of Methamphetamine Immunogen

D,L-Methamphetamine-N-Trifluoroacetamide 460 mg each of D- and L-methamphetamine were combined in a 25 mL roundbottom flask which was then cooled in an ice-water bath. Over a 15 minute period, 8 mL of trifluoroacetic anhydride was added gradually in 2 mL-portions to the stirred solution of amines. After stirring the solution for an additional 1 hour at 0° C., the cooling bath was removed and the pale yellow solution was stirred for 20 hours at room temperature. At the end of this period, the solution was poured over about 50 mg of ice and the resulting two-phase solution was diluted with 50 mL of diethylether into a separatory funnel. The aqueous layer was removed, and the organic phase was washed twice with 50 mL portions of water, once with 50 mL saturated aqueous sodium acetate, and again with 50 mL of water. After drying over sodium sulfate, evaporation of the diethyl ether gave 1.46 gm of a pale yellow oil. An analytical sample was isolated by preparative thin layer chromatography (TLC). Thus, 310 mg of the crude product was eluted with ethyl acetate on three 1 mm-thick, 20×20 cm silica gel plates. The upper dark bands at $R_f$ 0.78 were collected to afford 244 mg of a pale yellow liquid.

4'-Chlorosulfonyl-D,L-Methamphetamine-N-Trifluoroacetamide

D,L-Methamphetamine-N-trifluoroacetamide (244 mg) was dissolved in 3 mL chloroform in a 25 mL roundbottom flask and then cooled in an ice-water bath. Chlorosulfonic acid (3 mL.) was then added dropwise over 5 minutes to the stirred solution. After stirring for an additional 4 hours at this temperature, the pale yellow solution was added dropwise to 50 gm ice in a separatory funnel. The cold aqueous solution was extracted twice with 30 mL portions of chloroform. The organic extracts were combined, dried over sodium sulfate, and evaporated to afford 315 mg of a pale yellow oil.

Preparation of a 4'-Sulfonyl-D,L-Methamphetamine Immunogen

Bovine serum albumin, BSA, (134 mg.) was dissolved in 4.4 ml of 0.1M disodium phosphate (pH 8.0). After 5 minutes, 0.7 mL of dimethylformamide (DMF) was added to the protein solution. 4'-chlorosulfonyl-D,L-methamphetamine-N-trifluoroacetamide (52 mg) was dissolved in 500 ul of DMF and added on one portion to the aqueous solution of BSA. The initial turbidity disappeared after a brief period of stirring at room temperature. Conjugation was allowed to continue for a total of 24 hours at this temperature. After transferring the solution to a dialysis bag, the solution was dialyzed against 5 changes of deionized water (4 L each for 6 hours per change). Titration using picrylsulfonic acid revealed 31% hapten incorporation into the BSA. The contents of the dialysis bag were collected and diluted with 2 mL of methanol and 1.8 mL piperidine and allowed to stand for 18 hours at room temperature. The pH of this hydrolysis solution was approximately 12. Dialysis as described above was again performed, followed by lyophilization to give 91 mg of a fluffy white material.

EXAMPLE 2

Preparation of Amphetamine Immunogen

4-Nitro-D,L-Amphetamine-HCl

Fuming nitric acid (30 mls) was cooled to −35° C. D,L-Amphetamine sulfate (5.0 g) was added slowly (25 min.) with stirring. The reaction mixture (red) was stirred at this temperature for 2 hours, then allowed to warm to −15° C. (solution color changed from red to yellow), and stirred at −15° C. for 30 minutes. The solution was then poured into 125 ml ice water and extracted with 125 ml of benzene. The aqueous extract was made basic (pH=11) with 6M NaOH and extracted three times with 150 ml portions of benzene. There organic extracts were combined, dried over magnesium sulfate, and filtered. To the filtrate was added 250 ml of methanol, then HCl (gas) was bubbled into the stirred solution until solution pH was 3. Solvent was removed in vacuo and crude product recrystallized from ethanol-diethyl ether to afford 3.05 g of pale yellow powder.

4'-Nitro-D,L-Amphetamine-N-Trifluoroacetamide

4'-Nitro-D,L-Amphetamine.HCl (3.0 g) was dissolved in pyridine (40 mls), cooled to 0° C. and trifluoroacetic anhydride (9.8 mls) added. The solution was stirred at 0° C. for 2 hours, then poured into 200 ml ice water. The resulting precipitate was isolated via filtration and residual solvent removed in vacuo to afford 3.46 g of tan powder.

4'-Amino-D,L-Amphetamine-N-Trifluoroacetamide

4'-Nitro-D,L-Amphetamine-N-Trifluoroacetamide (600 mg) was dissolved in 50 ml absolute ethanol, 5% palladium on carbon (300 mg) was added, and the mixture hydrogenated under 21 psi of hydrogen in a Parr hydrogenator at room temperature for 2 hours. The catalyst was removed by filtration and solvent removed in vacuo to afford 421 mg of a pale yellow oil.

4'-Hemisuccinamido-D,L-Amphetamine-N-Trifluoroacetamide

4'-Amino-D,L-Amphetamine-N-Trifluoroacetamide (1.00 g) was dissolved in 7.0 ml chloroform, and succinic anhydride (614 mg) was added, followed by triethylamine (0.623 ml). The reaction was stirred for 2½ hours at room temperature under a nitrogen atmosphere, then diluted with 75 ml of water, pH adjusted to 4 with 1M HCl, and extracted 3 times with 100 ml portions of ethyl acetate. The ethyl acetate fractions were combined, dried over magnesium sulfate, and solvent removed in vacuo to afford 1.31 g of off-white solid.

4'-Succinamido-D,L-Amphetamine Immunogen

4'-Hemisuccinamido-D-L-Amphetamine-N-Trifluoroacetamide (50 mg) and N-Hydroxysuccinamide (20 mg) were dissolved in 0.500 ml of anhydrous dimethylformamide. Dicyclohexylcarbodiimide (36 mg) was added and the reaction stirred for about 2 hours and added dropwise to a solution of bovine serum albumin (125 mg) dissolved in 3.15 ml of 0.1M sodium phosphate (pH=7.5) and 1.35 ml of 1,4-dioxane. The resulting cloudy solution was stirred for 16 hours at room temperature, then transferred to dialysis tubing and dialyzed against 0.1M sodium phosphate (pH=7.5) (4 liters) for 2 hours, then against deionized water (2 changes of 4 liters each). The mixture was then centrifuged and supernatant lyophilized to afford 105 mg of a fluffy white powder. A portion of the product (45 mg) was dissolved in a solution of piperadine (2.5 mls), methanol (5 mls), and water (20 mls). After stirring for 45 minutes at room temperature, the solution was transferred to dialysis tubing, dialyzed against deionized H₂O (3 changes of 2 liters each), and lyophilized to afford 34 mg of fluffly white solid.

EXAMPLE 3

Preparation of Amphetamine Tracer

4-hydroxyphenylacetone

Hydrobromic acid (48%, 250 mL) was heated to approximately 120° C. Over a period of two minutes, a 9.85 g sample of 4-methoxyphenylacetone was added dropwise. After 15 minutes, the reaction mixture was chilled to 30° C. and diluted to 500 mL with distilled water. The resulting mixture was extracted twice with 250 mL portions of diethyl ether. The combined organic extracts were washed with brine, dried over magnesium sulfate, and the solvent was removed in vacuo. The resulting oil was purified immediately by column chromatography over silica gel, using 40% ethyl acetate and 60% hexane. Appropriate fractions were pooled and solvents removed in vacuo to yield a thick yellow oil.

4-(3-chloropropoxy)phenylacetone

A 4.50 g portion of p-hydroxyphenylacetone, prepared above, was dissolved in 80 mL of anhydrous dimethylformamide under a dry nitrogen atmosphere. With stirring 1.26 g of sodium hydride (as a 60% dispersion in oil) was added to the solution. After 3 minutes, 9.40 g of 1-chloro-3-iodopropane was quickly added. After stirring for approximately 18 hours, the reaction was diluted with 300 mL hexane and 100 mL diethyl ether. The resulting mixture was washed with distilled water, 5% sodium hydroxide solution, and brine. The remaining organic phase was dried and evaporated to dryness in vacuo. The yellow oil was purified by column chromatography over silica gel, using 22% ethyl acetate and 78% hexane. Appropriate fractions were pooled and solvents removed in vacuo to yield 3.06 g of a yellow oil.

4-(3-chloropropoxy)-1-(2-aminopropyl)benzene

A 1.36 g sample of 4-(3-chloropropoxy)phenylacetone, prepared above, was dissolved in 200 mL of methanol. To this was added 7.71 g of ammonium acetate followed by 0.76 g sodium cyanoborohydride with stirring. After 5 hours, the solvent was evaporated in vacuo, the residue was dissolved in 150 mL diethylether and 200 ml of 1N hydrochloric acid solution. The aqueous phase was separated and washed with a second portion of diethylether, basified to a pH of 10–12 with 6N sodium hydroxide, and extracted with three, 100 mL portions of diethylether. The basic ether extracts were combined, dried, and evaporated to dryness in vacuo to yield 1.11 g of a yellow oil.

4-(3-chloropropoxy)-1-(2-(N-t-butyloxycarbonyl)amino-propyl)-benzene

A 1.0 g sample of 4-(3-chloropropoxy)-1-(2-aminopropyl)benzene, prepared above, was dissolved in 50 mL of dichloromethane. To this was added, 1.92 g of di-t-butyl-dicarbonate. After stirring at room temperature for 18 hours, the solvent was removed in vacuo and the residue was dissolved in 35 ml diethylether and 15 mL of 5% sodium carbonate and then stirred for 2 hours. The organic phase was separated, washed with brine, dried over magnesium sulfate, filtered, and evaporated to dryness in vacuo. The resulting yellow oil was purified by column chromatography over silica gel using 20% ethyl acetate and 80% hexane. Appropriate fractions were pooled and solvents were removed in vacuo to yield 1.74 g of a white solid.

4-(3-Iodopropoxy)-1-(2-(N-t-butyloxycarbonyl)aminopropyl)benzene

A solution of 1.30 g of 4-(3-chloropropoxy)-1-(2-(N-t-butyloxycarbonyl)aminopropyl)-benzene in 40 mL anhydrous 2-butanone was prepared. To this was added 1.80 g sodium iodide. The resulting mixture was refluxed for 24 hours, cooled to room temperature, and diluted with 200 mL diethylether. The mixture was washed with 5% sodium thiosulfate solution, twice with brine, dried over magnesium sulfate, filtered, and evaporated to dryness in vacuo to yield 1.14 g of a white solid.

4-(3-Aminopropoxy)-1-(2-(N-t-butyloxycarbonyl)-aminopropyl)benzene

A 0.70 g portion of 4-(3-Iodopropoxy)-1-(2-(N-t-butyloxycarbonyl)-aminopropyl)benzene, prepared above, was dissolved in 10 mL of anhydrous diethylether. This ether solution was then added to a cold (4° C.) 250 mL saturated ammonia/ethanol solution.

The reaction was stirred and allowed to warm to room temperature. The mixture was resaturated with ammonia once a day for two days. After three full days, the solvent was removed in vacuo and the residue was suspended in 90 mL diethylether and 30 mL dichloromethane. The mixture was washed with 5% potassium carbonate (pH 12), washed with brine, dried over magnesium sulfate, filtered, and evaporated to dryness in vacuo. The residue was purified by column chromatography over silica gel using 84.5% dichloromethane, 15% methanol, and 0.5% acetic acid. Appropriate fractions were pooled and solvents removed in vacuo to yield 0.44 g of a thick, colorless oil.

4-[3-(5-Carboxyfluoresceinamidopropoxy)]-1-2-(N-t-butyl-oxycarbonyl)-aminopropyl)benzene A 119 mg portion of 5-carboxy fluorescein and 38 mg portion of N-hydroxysuccinimide was dissolved in 2 mL of anhydrous dimethylformamide. To this was added 68 mg of N,N'-dicyclohexylcarbodiimide. After stirring for 3 hours, a mixture of 100 mg 4-(3-aminopropoxy)-1-(2-(N-t-butyloxy-carbonyl)-aminopropyl)-benzene, 1 mL of anhydrous dimethylformamide, and 100 microliters triethylamine were added to the reaction mixture. After 18 hours of stirring, the solvents were removed in vacuo to yield an orange solid. The product was purified on four, 1.0 mm C18 reversed phase preparative thin layer chromatography plates developed in 69.5% methanol, 30.0% distilled water, and 0.5% acetic acid. The band of $R_f$ of 0.14 was collected and eluted with methanol to yield 115 mg of an orange solid.

4-[3-(5-Carboxyfluoresceinamidopopoxy]-1-(2-aminopropyl)benzene

The entire 115 mg yield of product from Example 22 was dissolved in 3 mL dichloromethane. With stirring 2 mL of trifluoroacetic acid was added dropwise. After approximately 10 minutes, the solvents were removed in vacuo, residue was dissolved in 5 mL methanol and 100 microliters triethylamine and solvents removed in vacuo again. The residue was suspended in 2 ½ mL methanol and triethylamine was added until the solid completely dissolved. The product was then purified on four 1.0 mm C18 reversed phase preparative thin layer chromatography plates developed in 69.5% methanol, 30.0% distilled water, and 0.5% acetic acid. The band at $R_f$ of 0.69 was collected and eluted with methanol to yield product.

EXAMPLE 4

Preparation of Methamphetamine Tracer Dimethyl p-Phenylenediacetate

A 19.42 g portion of 1,4-phenylene diacetic acid was suspended in 200 ml of methanol. To this was added 20 mL trimethyl orthoformate and 16 mL of methanol saturated with hydrogen chloride. After stirring for 3 hours at room temperature, the solvents were removed in vacuo. The residue was stirred with 1.5 l of hexane, mixed with 400 mL saturated sodium bicarbonate solution and decanted into a separatory funnel leaving undissolved solids behind. The two phases were separated, the organic phase was washed with a second 400 ml saturated sodium bicarbonate solution and then with 200 mL of brine. The resulting organic phase was dried over magnesium sulfate, filtered, and evaporated to dryness in vacuo to yield a white powder.

Methyl 4-Carboxymethylphenylacetate

Eight grams of dimethyl p-phenyleneacetate, prepared above, was dissolved in 120 mL of methanol. To this was added 28.8 mL of 1M sodium hydroxide solution and stirred at room temperature for 3 hours. The reaction mixture was then quenched by the addition of 8 mL acetic acid and evaporated to dryness in vacuo. The residue was diluted with 800 mL of saturated sodium bicarbonate solution and washed twice with 400 mL portions of hexane. The remaining aqueous phase was acidified to a pH of 1 and extracted three times with 200 mL portions of dichloromethane. The combined organic extracts were washed with brine, dried over magnesium sulfate, filtered, and evaporated to dryness in vacuo to yield 3.71 g of a white solid.

4-(Carbomethoxymethyl)phenylacetyl chloride

A 3.04 g portion of methyl 4-carboxymethylphenylacetate, prepared above, was dissolved in 50 mL of anhydrous tetrahydrofuran. After the addition of 2.5 mL oxalyl chloride, the mixture was stirred for 4 hours. The solvents were evaporated under a stream of dry nitrogen as the flask was warmed to 45° C. Any remaining solvent or oxalyl chloride was then removed under high vacuum; the product was used without further purification.

Methyl 4-(2-oxopropyl)-phenylacetate

A sample of copper (I) iodide was heated at 120° C. for 2 hours, then cooled to room temperature in a vacuum dessicator. Under a dry nitrogen atmosphere 50 mL anhydrous tetrahydrofuran was added to 8.35 g of the copper iodide. The suspension was chilled to −10° C., then 52 mL of 1.7M methyllithium in ether was quickly added dropwise. The entire yield of the 4(carbomethoxymethyl)phenylacetyl acid chloride was dissolved in 20 mL anhydrous tetrahydrofuran and quickly added to the reaction mixture as the temperature was lowered to −78° C. After 30 minutes the reaction was quenched with 5 mL of methanol, warmed to room temperature, diluted with 15 mL methanol, and then diluted to 1 liter with diethylether. The reaction was washed with saturated ammonium chloride and ammonium hydroxide, 10% ammonium chloride and ammonium hydroxide, and once with brine. The organic phase was dried and evaporated to dryness in vacuo. The residue was purified by column chromatography over silica gel using 30% ethylacetate and 70% hexane. Appropriate fractions were pooled and solvents removed in vacuo to yield 0.60 g of product.

Methyl 4-(2-methylaminopropyl)phenylacetate

To 25 mL of methanol 0.59 g of methyl 4-(2-oxopropyl)phenylacetate, prepared above, was added and dissolved. Then with stirring the following were added: 2.0 g methylamine hydrochloride, 0.3 g sodium cyanoborohydride, and 0.3 mL of triethylamine. After approximately 12 hours an additional 0.1 g of sodium cyanoborohydride was added to the mixture. After 3 hours more, the reaction was diluted with 100 mL of 0.1M hydrochloric acid, washed with diethylether, and the resulting aqueous phase was basified to a pH of 12 by addition of 5 mL portions of 1N sodium hydroxide solution. This was extracted three times with 100 mL portions of diethylether, combined extracts washed with brine and dried. The solvents were removed in vacuo to yield 0.44 g of a light yellow oil.

Methyl 4-(2-(N-t-butoxycarbonyl)-N-methylaminopropyl)phenyl-acetate

A 0.44 g portion of methyl, 4-(2-methylaminopropyl)phenylacetate, prepared above, was dissolved in 20 mL of methylene chloride. To this solution was added 2.0 g di-t-butyldicarbonate and 0.45 mL triethylamine. After 14 hours the reaction was diluted with 100 mL of diethylether and stirred with 40 mL of saturated sodium bicarbonate solution. After 3 hours an additional 100 mL of diethylether was added, the organic phase was then separated and washed twice with 50 mL portions of brine. The resulting organic phase was dried and evaporated in vacuo. The resulting yellow oil was purified by column chromatography over silica gel using 35% ethylacetate and 65% hexane. The appropriate fractions were pooled and solvents evaporated in vacuo to yield 0.39 g of a viscous oil.

4-(2-(N-t-butoxycarbonyl)-N-methylaminopropyl)-phenylacetic acid

A 320 mg portion of methyl 4-(2-(N-t-butoxycarbonyl-N-methylamino-propyl))phenylacetate, prepared above, was dissolved in 6 mL of dioxane. To this, 3 mL of 1N sodium hydroxide solution was added. After 10 minutes of stirring, 3 mL of acetic acid was added to the mixture, followed by 100 ml of diethylether. This was washed once with 50 ml of brine and the brine was extracted with an equal volume of dichloromethane. The ether and dichloromethane extracts were combined, dried over magnesium sulfate, filtered, and evaporated to dryness in vacuo to yield 360 mg of a light oil.

N-(Methylfluoresceinyl)-4-[2-(N-t-butyloxycarbonyl)-methylaminopropyl]phenylacetamide A 104 mg portion of 4-[2-(N-t-butoxycarbonyl)methylaminopropyl]phenyl acetic acid, prepared above, and 94 mg of Woodward's Reagent K were dissolved in 3 mL of anhydrous dimethylformamide and 0.05 mL triethylamine. After 1 hour of stirring at room temperature, 134 mg 4'-aminomethylfluorescein dihydrochloride and 0.1 mL triethylamine were added. The mixture was stirred for 2 hours at room temperature and then stored in a freezer overnight. The mixture was then warmed and stirred at room temperature for 3 hours before the solvent was removed in vacuo. The resulting orange solid was purified on four, 1.0 mm C18 reversed phase preparative thin layer chromatography plates developed in 74.5% methanol, 25% distilled water, and 0.5% acetic acid. The band at $R_f 0.21$ was collected and eluted with methanol to yield product.

N-(Methylfluoresceinyl)-p-2-methylaminopropyl-phenylacetamide

The entire yield of the above-formed product was dissolved in 4 mL of dichloromethane. While stirring two mL of trifluoroacetic acid was stirred into the solution, and after 5 minutes the solvent was removed in vacuo. With stirring, the residue was dissolved in 25 mL methanol and triethylamine was added dropwise until a dark orange color had formed. The solvent was removed again in vacuo and the residue dissolved in methanol. The product was purified on four, 1.0 mm C18 reversed-phase preparative thin layer chromatography plates developed in 64.5% methanol, 35.0% distilled water, and 0.5% acetic acid. The band at $R_f 0.50$ was collected and eluted with methanol to yield product.

EXAMPLE 5

Amphetamine/Methamphetamine Assay

A. Reagents (1) Pretreatment Solution—A solution containing about 0.125 sodium periodate. (pH 4.5).
(2) Tracer: Consisting of Compound I prepared in Example 4 and Compound II prepared in Example 3. Each compound is in 0.1M sodium phosphate buffer at pH 7.5 containing 0.01% w/v bovine gamma globulin, and 0.1% w/v sodium azide.
(3) Antibody: Rabbitt or sheep antiserum consisting of antiserum raised against amphetamine and methamphetamine appropriately diluted in 0.1M sodium phosphate buffer, 0.1% sodium azide and 2% ethylene glycol.
(4) Diluent buffer: 0.1M sodium phosphate, pH 7.5, 0.1% bovine gamma globulin and 0.1% sodium azide.
(5) Calibrators: charcoal stripped human urine preserved wth 0.1% sodium azide having d,l-amphetamine levels as follows: 0.00, 0.23, 0.38, 0.83, 1.58, 3.08 ug/ml.
(6) Controls: charcoal stripped normal human urine preserved with 0.1% sodium azide, containing 0.68 or 2.08 ug/ml of d,l-amphetamine.
(7) Wash: A solution containing about 0.125M sodium periodate.

All polarized fluorescence measurements were made using the Abbott TDx ® Clinical Analyzer.

B. Assay Protocol (1) Equal portions of an unknown sample and pretreatment solution are pipetted into the predilute well. A sufficient volume of diluent buffer is added to raise the volume to 500 ul. This mixture is incubated for 4-6 minutes.
(2) A sample from the predilute well and 25 ul of antibody is pipetted into the cuvette. A background intensity reading is taken.
(3) 25 ul each of tracer and antibody, and a sample from the predilute well, is added to the cuvette. Sufficient diluent buffer is added to raise the final volume to 2.0 mls.
(4) The fluorescence polarization due to tracer binding to the antibody is obtained by subtracting the polarized fluorescence intensities of the background from the final polarized fluorescence intensities of the mixture.
(5) The polarization values obtained are inversely proportional to the amphetamine and/or methamphetamine concentration of each sample.
(6) The polarization value for a sample is compared to a standard curve prepared using calibrators of known amphetamine or methamphetamine content.

EXAMPLE 6

Sodium Periodate Pretreatment

Samples containing 50 and 100 ug/ml of ephedrine were assayed with the Abbott TDx ® Clinical Analyzer with and without the preincubation treatment described in Example 5B above. The assay utilized the above-described amphetamine/methamphetamine tracers and antibodies. Results are presented in Table II below:

TABLE II

| μg/ml Ephedrine | Polarization |
|---|---|
| 50 w/pretreatment | 216.09 |
| 50 w/o pretreatment | 79.75 |
| 100 w/pretreatment | 208.19 |
| 100 w/o pretreatment | 70.45 |

The above results illustrate that sodium periodate treatment of samples without the addition of pH raising constituents, such as base, is effective in eliminating β-hydroxyphenethylamine cross-reactivity and is useful for such purpose in amphetamine/methamphetamine fluorescence polarization assays.

What is claimed is:

1. In a method for determining phenethylamines in a test sample of biological fluid by fluorescence polarization assay the improvement consisting of:
pretreating said sample with an effective amount of an aqueous periodate solution having a pH from about 4.0 to about 7.5 for a period of time sufficient to eliminate β-hydroxyphenethylamine cross reactants.

2. The improvement of claim 1 wherein said sample is pretreated for about 1 to about 10 minutes.

3. The improvement of claim 1 wherein said aqueous periodate solution comprises from about 0.1 to about 0.25 Molar sodium periodate.

4. The improvement of claim 1 wherein said sample is pretreated for about 4 to about 5 minutes.

5. The improvement of claim 1 wherein said pretreatment is carried out at a temperature in a range from about 31° to about 36° C.

6. A method for determining amphetamine and methamphetamine in a test sample of biological fluid by fluorescence polarization assay comprising the steps of:
(a) pretreating said sample with an effective amount of an aqueous periodate solution having a pH from about 4.0 to 7.5 for a period of time sufficient to eliminate β-hydroxyphenethylamine cross reactants to amphetamine and methamphetamine;
(b) intermixing said pretreated sample with a salt of a first tracer of the formula:

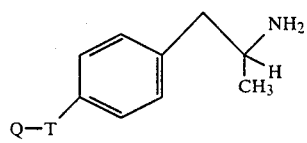

and a second tracer of the formula:

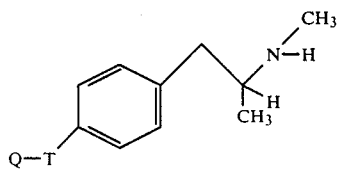

wherein Q is a fluorescein or a fluorescein derivative, T is
SO₂, NH, HN(CH₂)₃O, COCH₂, CO(CH₂)₂CONH, HN(CH₂)₂ or HN(CH₂)₂ NHCOCH₂, and
a first antibody capable of specifically recognizing and binding amphetamine and said first tracer thereof; and a second antibody capable of specifically recognizing and binding methamphetamine and said second tracer thereof; and
(c) then determining the amount of each tracer bound to said first and second antibodies by fluorescence polarization techniques as a measure of the amount of amphetamine and methamphetamine in the sample.

7. The method of claim 6, wherein said fluorescein derivative of said first tracer is a carboxyfluorescein and said fluorescein derivative of said second tracer is 4'-aminomethylfluorescein.

8. The method of claim 6, wherein said first tracer has a formula:

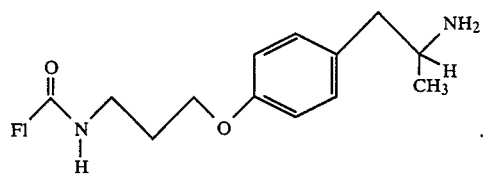

9. The method of claim 6, wherein said second tracer has a formula:

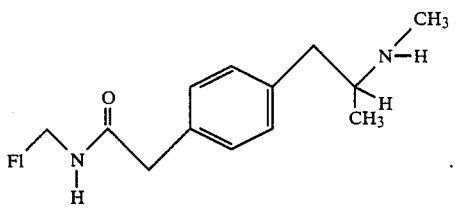

10. A stabilized reagent kit useful in determination of amphetamine and methamphetamine comprising:
(a) a pretreatment solution having an amount of aqueous sodium periodate effective in eliminating β-hydroxyphenethylamine crossreactivity to amphetamine and methamphetamine;
(b) a fluorescence reagent having salts of a first and a second tracer, said first tracer being a fluorescein or fluorescein derivative compound bound to a ligand analog of amphetamine and said second tracer being a fluorescein or fluorescein derivative compound bound to a ligand analog of methamphetamine; and
(c) an antibody reagent having a first antibody capable of specifically recognizing amphetamine and said first tracer thereof and a second antibody capable of specifically recognizing methamphetamine and said second tracer thereof.

11. The stabilized reagent kit of claim 10, further comprising an aqueous wash solution having from about 0.1 to about 0.25 molar sodium periodate.

12. The stabilized reagent kit of claim 10, wherein said first tracer has a formula

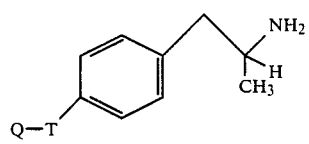

and said second tracer has a formula

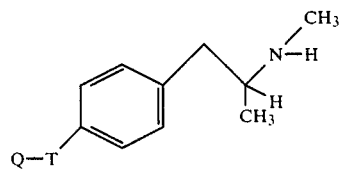

wherein Q is said fluorescein or fluorescein derivative; T is SO₂, HN, HN(CH₂)₃O, COCH₂, CO(CH₂)₂ CONH, HN(CH₂)₂ or HN(CH₂)₂NHCO CH₂.

13. The stabilized reagent kit of claim 10, wherein said first tracer has a formula

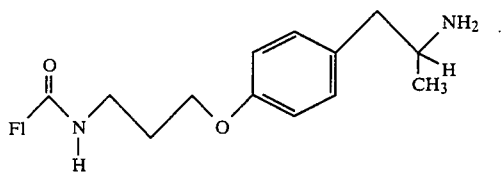

and said second tracer has a formula

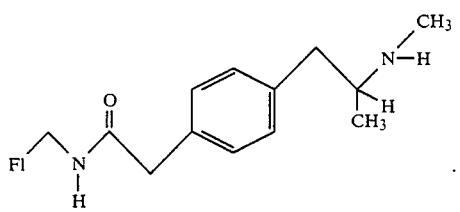

14. The stabilized reagent kit of claim 10, wherein said first antibody is raised in response to an immunogen having the structure:

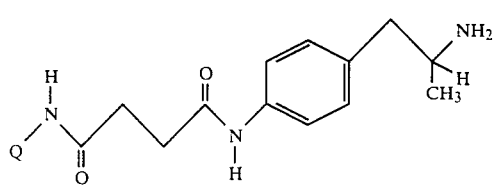

and said second antibody is raised in response to an immunogen having the structure:

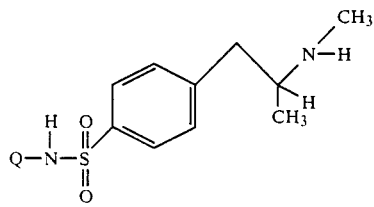

wherein Q is a poly(amino acid) or poly(amino acid) derivative.

15. A method for determining amphetamine and methamphetamine in test samples of biological fluid by fluorescence polarization assay utilizing an automatic assay apparatus having a sample and reagent dispensing means comprising the steps of:
 (a) pretreating a sample to eliminate β-hydroxyphenethylamine cross-reactivity using only an effective amount of an aqueous periodate solution having a pH from about 4.0 to 7.5 for a period of time sufficient to eliminate said β-hydroxyphenethylamine cross-reactivity;
 (b) intermixing said pretreated sample with a salt of a first tracer of the formula:

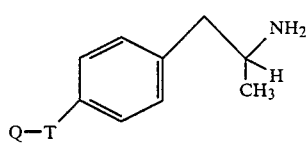

and a second tracer of the formula:

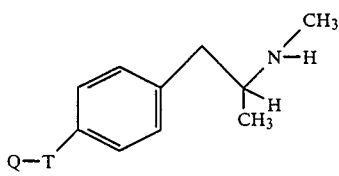

wherein Q is fluorescein or a fluorescein derivative, T is $SO_2$, NH, $HN(CH_2)_3O$, $COCH_2$, $CO(CH_2)_2CONH$, $HN(CH_2)_2$ or $HN(CH_2)_2NHCOCH_2$, and
a first antibody capable of specifically recognizing and binding amphetamine and said first tracer thereof; and a second antibody capable of specifically recognizing and binding methamphetamine and said second tracer thereof;
 (c) determining the amount of each tracer bound to said first and second antibodies by fluorescence polarization techniques as a measure of the amount of amphetamine and methamphetamine in the sample; and
 (d) washing said dispensing means in a 0.1 to 0.25M aqueous periodate solution to minimize sample adhesion to said dispensing means.

16. The method of claim 15, wherein said dispensing means is a probe which is washed in said periodate solution.

* * * * *

UNITED STATES PATENT AND TRADEMARK OFFICE
CERTIFICATE OF CORRECTION

PATENT NO. : 4,868,132

DATED : September 19, 1989

INVENTOR(S) : Paul J. Brynes, et al.

It is certified that error appears in the above-identified patent and that said Letters Patent is hereby corrected as shown below:

On the title page, under item [19] and in item [75] Inventors:, change "Byrnes" to --Brynes--.

Column 2, Line 37, change "pH raising" to --pH-raising--.

Column 4, Line 63, change "Flourescein" to --Fluorescein--.

Column 7, Line 49, change "$CH_2CL_2$" to --$CH_2Cl_2$--.

Column 7, Line 52, change "4'-aminomethylfluorecein" to --4'aminomethylfluorescein--.

Column 8, Lines 35-36, change "mehtamphetamine" to --methamphetamine--.

Column 10, Line 25, change "amimo" to --amino--.

Column 12, Line 67, change "d,1 amphetamine" to --d,1-amphetamine--.

Column 15, Line 4, change "N-Hydroxysuccinamide" to --N-hydroxysuccinimide--.

Column 15, Line 17, change "piperadine" to --piperidine--.

Column 17, Line 10, change: "4-[3-(5-Carboxyfluoresceinamidopopoxy]-1-(2-amino-" to --4-[3-(5-Carboxyfluoresceinamidopropoxy]-1-(2-amino---.

Column 17, Line 47, change "p-phenyleneacetate" to --p-phenylenediacetate--.

Column 18, Line 9, change "dessicator" to --desiccator--.

Column 19, Line 64, change "Rabbitt" to --Rabbit--.

UNITED STATES PATENT AND TRADEMARK OFFICE
CERTIFICATE OF CORRECTION

PATENT NO. : 4,868,132

DATED : September 19, 1989

INVENTOR(S) : Paul J. Brynes, et al.

It is certified that error appears in the above-identified patent and that said Letters Patent is hereby corrected as shown below:

Column 20, Line 25, change "is" to --are--.

Figure 7, change:

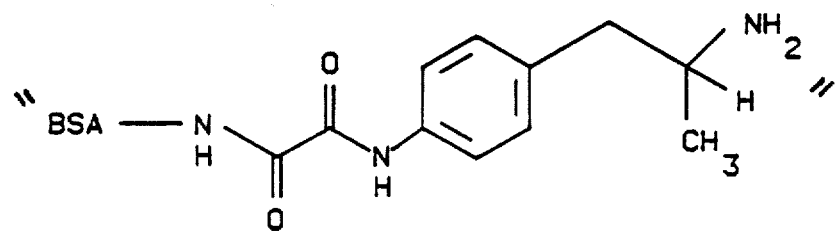

to

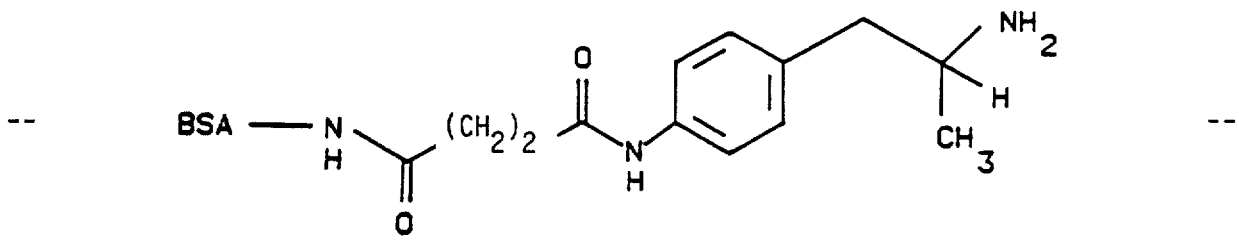

UNITED STATES PATENT AND TRADEMARK OFFICE
CERTIFICATE OF CORRECTION

PATENT NO. : 4,868,132

DATED : September 19, 1989

INVENTOR(S) : Paul J. Brynes, et al.

It is certified that error appears in the above-identified patent and that said Letters Patent is hereby corrected as shown below:

Column 1, Line 65, change "methamohetamine" to --methamphetamine--.

Column 2, Line 53, insert --a-- between "comprising" and "First".

Column 4, Line 11, change "antibodied" to --antibodies--.

Column 4, Line 16, delete "cl" and skip a line before "DETAILED DESCRIPTION OF THE INVENTION".

Column 16, Lines 9-10 change:

"4-(3-chloropropoxy)-1-(2-(N-t-butyloxycarbonyl-
)amino-propyl)-benzene"

to --4-(3-chloropropoxy)-1-(2-(N-t-butyloxycarbonyl)
amino-propyl)-benzene--

Claim 5, Line 3, change "31" to --31°C--.

Claim 6, Line 46, insert --a linking group selected from-- after "is".

Column 22, Line 23, insert --the-- between "in" and "determination".

Column 22, Line 66, change "$HN(CH_2)_2NHCO\ CH_2$" to --$HN(CH_2)_2NHCOCH_2$--.

UNITED STATES PATENT AND TRADEMARK OFFICE
CERTIFICATE OF CORRECTION

PATENT NO. : 4,868,132

DATED : September 19, 1989

INVENTOR(S) : Paul J. Brynes, et al.

It is certified that error appears in the above-identified patent and that said Letters Patent is hereby corrected as shown below:

Column 20, Line 22, change "is" to --are--.

Signed and Sealed this

Third Day of March, 1992

Attest:

HARRY F. MANBECK, JR.

Attesting Officer

Commissioner of Patents and Trademarks